US00PP27144P3

(12) United States Plant Patent
Grosser

(10) Patent No.: US PP27,144 P3
(45) Date of Patent: Sep. 13, 2016

(54) SWEET ORANGE TREE NAMED 'B9-65'

(50) Latin Name: *Citrus sinensis*
Varietal Denomination: B9-65

(71) Applicant: Florida Foundation Seed Producers, Inc., Marianna, FL (US)

(72) Inventor: Jude W. Grosser, Winter Haven, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 91 days.

(21) Appl. No.: 14/121,945

(22) Filed: Nov. 5, 2014

(65) Prior Publication Data

US 2016/0128252 P1 May 5, 2016

(51) Int. Cl.
*A01H 5/08* (2006.01)

(52) U.S. Cl.
USPC ..... Plt./202

(58) Field of Classification Search
USPC ..... Plt./202
See application file for complete search history.

(56) References Cited

PUBLICATIONS

Grosser et al., "Somaclonal Variation in Sweet Orange: Practical Applications for Variety Improvement and Possible Causes," pp. 219-234, in: Kahn, I.H. (Ed.). Citrus Genetics, Breeding and Biotechnology. CAB International, 2007.
Larkin et al., "Somaclonal variation—a novel source of variability from cell cultures for plant improvement," *Theor Appl Genet* 60:197-214, 1981.

*Primary Examiner* — Annette Para
(74) *Attorney, Agent, or Firm* — Dentons US LLP

(57) ABSTRACT

A new and distinct sweet orange clone, 'B9-65' was produced via adventitious shoot induction from a nucellar seedling internode stem segment. 'B9-65' is a vigorous tree that produces standard 'Valencia'-type sweet orange fruit that is characterized by high fruit yield and high soluble solids content. The fruit size of 'B9-65' is larger than that for standard Valencia orange while having a similar fruit maturation date.

4 Drawing Sheets

Latin name of the genus and species of the plant claimed: *Citrus sinensis.*

Variety denomination: 'B9-65'.

BACKGROUND OF THE INVENTION

The invention relates to a new and distinct variety of sweet orange named 'B9-65'. 'B9-65' is a vigorous tree that produces standard 'Valencia'-type sweet orange fruit, and is superior to other Valencia and Valencia-like clones for yield and juice quality, with a standard 'Valencia' fruit maturation date. In Florida, quality fruit of 'B9-65' can generally be harvested from mid-February through May, depending on environmental conditions.

'B9-65' originated as a somaclone of 'Valencia' sweet orange regenerated via adventitious shoot induction from a nucellar seedling stem piece obtained from standard Valencia (*Citrus sinensis* L. Osbeck) in 1987. Somaclonal variation is defined as variability in plants regenerated from tissue culture that is either induced or uncovered by a tissue culture process. Most somaclonal variation is negative, but if enough plants are examined, positive changes can usually be recovered. Somaclonal variation has been a primary source of genetic variation in sweet orange exploited in citrus improvement programs.

The first asexual reproduction of 'B9-65' involved grafting of the original tree to 'Carrizo' citrange rootstock and planting at a collaborative research block in Indiantown, Martin County, Fla. in 1989. Vegetative budwood was then cut from the tree and successfully grafted onto 'Carrizo' in 2000 in Lake Alfred, Fla. The second generation tree was planted in Winter Park, Fla., and has demonstrated true-to-typeness.

SUMMARY OF THE INVENTION

'B9-65' was selected on the basis of high fruit yield and high soluble solids content in fruit, based on five years of data from a replicated trial planted in Winter Park, Fla. (Tables 1 and 2). The trial included both juvenile and mature clones of commercial 'Valencia', a commercial clone of 'Rhode Red' Valencia, and numerous other seedling introductions and somaclones (30 selections were evaluated). 'B9-65' ranked number one in cumulative yield over five consecutive harvests and was in the top five every season for high soluble solids in the juice. The average size of fruit of 'B9-65' is also larger than that of standard Valencia, which simplifies harvesting. 'B9-65' has a typical 'Valencia' harvest date (approximately mid-February through May).

The following are the most outstanding and distinguishing characteristics of this new cultivar 'B9-65' when grown under normal horticultural practices in Florida.

1. The tree bears superior yields of delicious low-seeded, large-sized 'Valencia' sweet orange fruit with high juice content and quality.
2. The tree may be used both fresh or for processing because it bears low-seeded fruit with good fresh fruit and juice quality during the typical 'Valencia' season in Florida.

TABLE 1

Yield of boxes/tree of late season sweet orange selections on 'Carrizo' citrange rootstock planted 15' × 25' at Water Conserv II, Winter Garden, Fl., planted March, 2000.

| Late season selections | 2005-06 | 2006-07 | 2007-08 | 2008-09 | 2009-10 | Cumulative Yield | Cumulative Rank |
|---|---|---|---|---|---|---|---|
| 'B-9-65' | 2.21 | 1.28 | 5.38 | 1.40 | 4.80 | 15.06 | 1 |
| 'Appleby' | 2.46 | 0.98 | 4.61 | 1.82 | 4.91 | 14.78 | 2 |
| 'T-4-43' | 1.80 | 1.02 | 4.40 | 0.73 | 5.81 | 13.76 | 3 |
| 'T-2-25' | 2.08 | 1.27 | 4.15 | 1.08 | 4.68 | 13.26 | 4 |
| 'S441-54-3' (Juv. 10-12-7) | 2.27 | 1.24 | 4.40 | 0.83 | 4.38 | 13.13 | 5 |
| 'T-3-62' | 1.59 | 1.58 | 3.80 | 1.21 | 4.52 | 12.70 | 6 |
| 'S822-111-5' (Mat.10-12-7) | 1.94 | 1.53 | 3.13 | 2.31 | 3.72 | 12.62 | 7 |
| 'B-8-66' | 2.03 | 1.18 | 3.88 | 1.23 | 4.25 | 12.58 | 8 |
| 'B-10-81' | 1.89 | 1.29 | 4.25 | 1.18 | 3.94 | 12.56 | 9 |
| 'B-6-68' | 2.13 | 1.11 | 4.21 | 1.00 | 4.10 | 12.53 | 10 |
| 'B-12-71' | 2.25 | 0.75 | 4.19 | 1.13 | 4.20 | 12.52 | 11 |
| 'Jenner' | 2.08 | 1.18 | 4.52 | 1.18 | 3.48 | 12.44 | 12 |
| 'Natal' | 1.48 | 1.46 | 4.07 | 1.04 | 4.27 | 12.32 | 13 |
| 'Smith' | 2.11 | 0.99 | 3.93 | 1.01 | 4.26 | 12.30 | 14 |
| 'T-1-13' | 2.35 | 0.84 | 4.28 | 0.91 | 3.80 | 12.18 | 15 |
| 'T-1-23' | 1.82 | 0.70 | 4.07 | 1.42 | 4.18 | 12.18 | 16 |
| 'T-2-62' | 1.80 | 1.06 | 3.82 | 1.22 | 4.18 | 12.08 | 17 |
| 'Frost' | 2.14 | 0.79 | 4.52 | 0.84 | 3.77 | 12.06 | 18 |
| 'B-8-76' | 1.84 | 0.89 | 4.43 | 0.66 | 4.13 | 11.96 | 19 |
| 'T-1-25' | 1.61 | 0.69 | 4.61 | 0.43 | 4.38 | 11.72 | 20 |
| 'T-1-26' | 1.66 | 0.72 | 4.29 | 0.81 | 4.22 | 11.70 | 21 |
| 'T-1-33' | 1.62 | 0.67 | 3.75 | 0.77 | 4.47 | 11.27 | 22 |
| 'Rhode Red' Valencia | 1.51 | 1.49 | 3.47 | 1.57 | 3.19 | 11.22 | 23 |
| Valencia 'SF8-2-35' | 1.72 | 1.19 | 3.11 | 1.88 | 3.31 | 11.21 | 24 |
| 'B-10-68' | 1.82 | 0.96 | 4.12 | 1.07 | 3.20 | 11.16 | 25 |
| 'Vernia' | 1.35 | 1.34 | 3.18 | 1.29 | 3.12 | 10.28 | 26 |
| Valencia 'SF11-1-69' | 1.54 | 1.17 | 2.06 | 1.47 | 3.40 | 9.64 | 27 |
| 'B-10-62' | 0.99 | 0.74 | 2.58 | 1.25 | 2.27 | 7.82 | 28 |
| Valencia 'SF9-1-86' | 0.93 | 0.73 | 2.04 | 1.05 | 2.83 | 7.58 | 29 |
| 'B-6-66' | 0.82 | 1.06 | 1.48 | 1.03 | 2.38 | 6.77 | 30 |

TABLE 2

Juice quality of late season sweet orange selections collected Apr. 23, 2010 on 'Carrizo' citrange rootstock planted 15' × 25' at Water Consery II, Winter Garden, FL.

| Late season selections | Juice content, % | Soluble solids conc., % | Acid, % | SS/A ratio | Pounds solids/box | Color number |
|---|---|---|---|---|---|---|
| 'B-10-62' | 48.50 | 13.55 | 0.94 | 14.37 | 5.89 | 39.0 |
| 'B-6-66' | 44.38 | 15.05 | 0.95 | 15.84 | 5.93 | 37.3 |
| 'B-6-68' | 54.46 | 12.84 | 0.86 | 15.01 | 6.29 | 38.4 |
| 'B-8-66' | 53.81 | 13.11 | 0.87 | 15.11 | 6.35 | 38.3 |
| 'B-9-65' | 53.03 | 12.91 | 0.84 | 15.32 | 6.16 | 38.1 |
| 'Frost' | 46.35 | 12.69 | 0.73 | 17.32 | 5.29 | 38.6 |
| 'Natal' | 52.22 | 13.00 | 0.90 | 14.31 | 6.05 | 38.1 |
| 'Rhode Red' Valencia | 53.94 | 12.63 | 0.82 | 15.37 | 6.13 | 39.5 |
| 'S441-54-3' (Juv. 10-12-7) | 54.84 | 13.06 | 0.87 | 14.94 | 6.45 | 38.5 |
| 'Smith' | 52.40 | 13.09 | 0.86 | 15.23 | 6.18 | 38.3 |
| 'T-1-13' | 51.86 | 12.83 | 0.88 | 14.56 | 5.99 | 38.0 |
| 'T-1-23' | 51.73 | 12.65 | 0.78 | 16.30 | 5.89 | 38.6 |
| 'T-1-33' | 51.55 | 12.60 | 0.84 | 15.06 | 5.85 | 38.4 |
| 'T-2-25' | 51.25 | 12.82 | 0.85 | 15.10 | 5.90 | 38.3 |
| 'T-2-62' | 51.50 | 12.98 | 0.85 | 15.29 | 6.01 | 38.4 |
| 'T-3-62' | 52.82 | 12.62 | 0.84 | 15.04 | 6.00 | 38.6 |
| 'Vernia' | 48.03 | 13.77 | 0.66 | 21.03 | 5.95 | 39.2 |
| Mean | 51.44 | 13.07 | 0.84 | 15.60 | 6.02 | 38.5 |
| LSD | 3.46 | 0.54 | 0.05 | 0.95 | 0.41 | 0.98 |

BRIEF DESCRIPTION OF THE DRAWINGS

'B9-65' is illustrated by the accompanying photographs, which show the tree's form, foliage, and fruit. The colors shown are as true as can be reasonably obtained by conventional photographic procedures.

DETAILED BOTANICAL DESCRIPTION

Phenotypic Description of *Citrus sinensis* 'B9-65'

Figure 1:
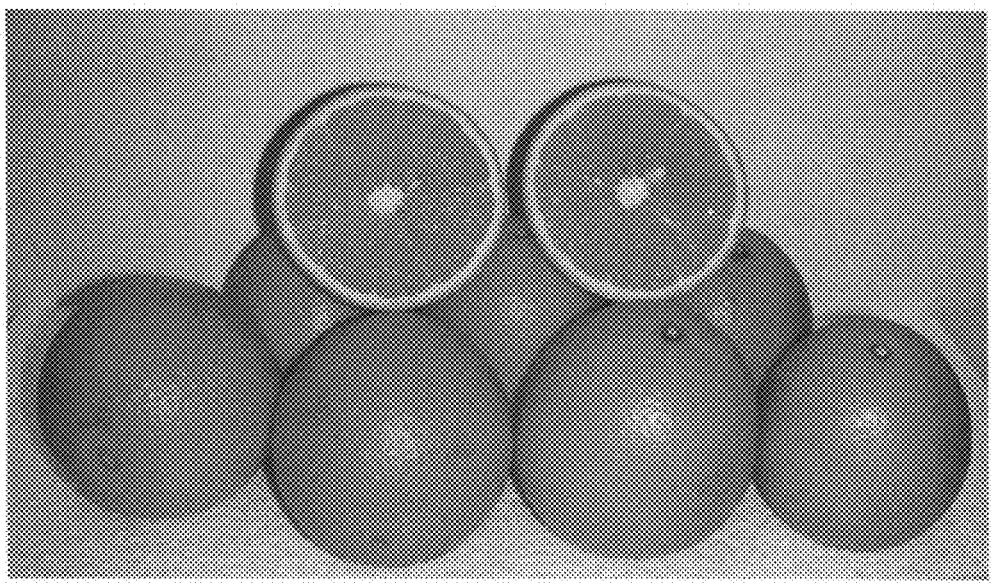
FIG. 1—Shows a close-up of whole and cut fruit of 'B9-65'.
Figure 2:
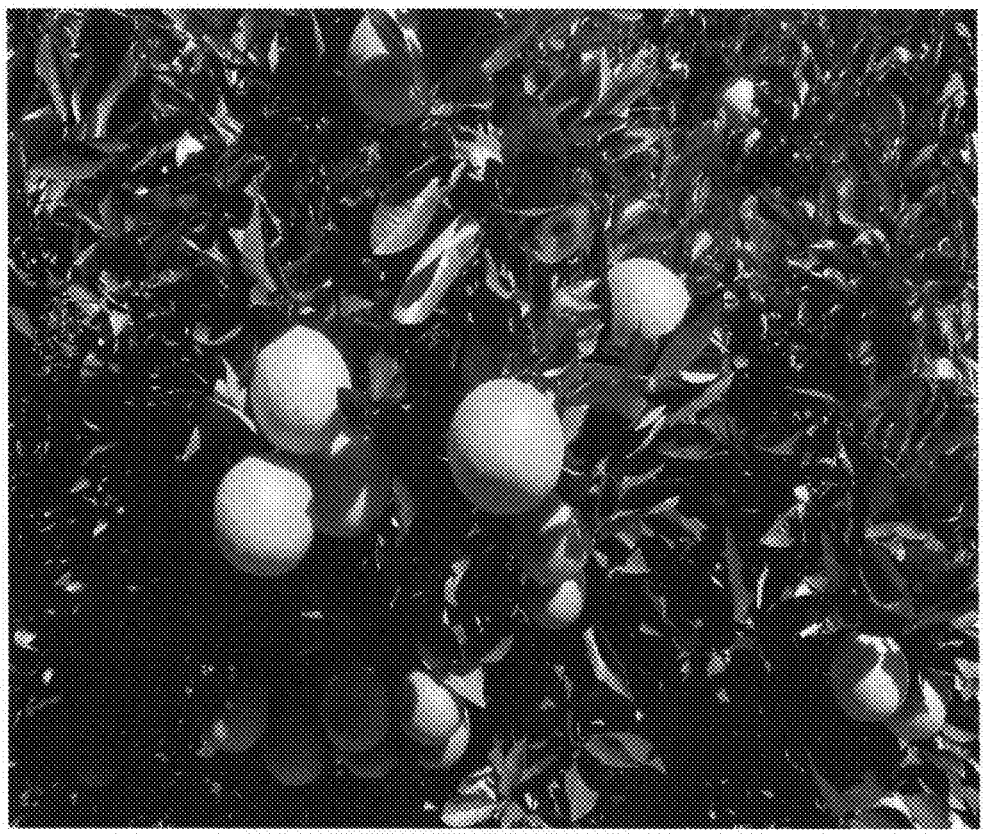
FIG. 2—Shows mature fruit of 'B9-65' hanging on the tree in Winter Garden, Fla.
Figure 3:
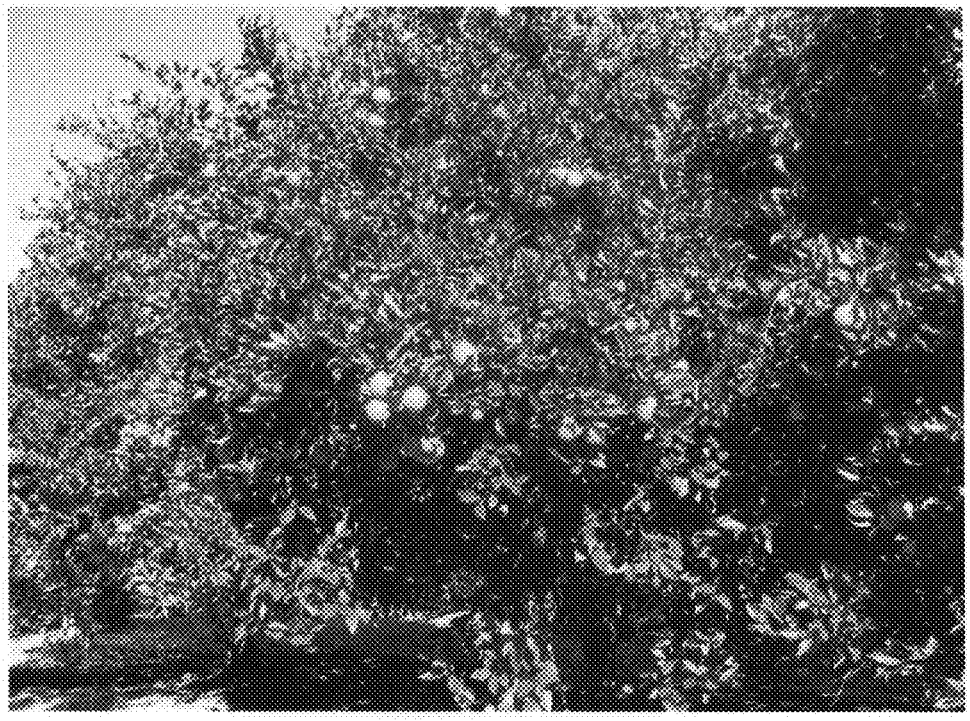
FIG. 3—Shows 'B9-65' tree on 'Carrizo' citrange rootstock (December, 2010).
Figure 4:
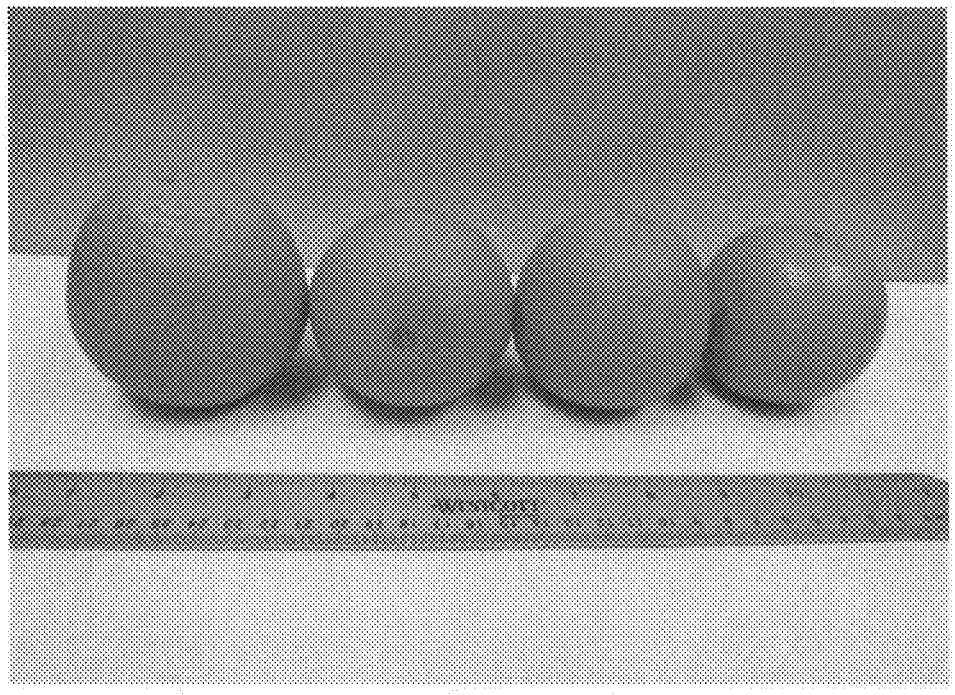
FIG. 4—Shows the size of whole fruit of 'B9-65'.

The following detailed description sets forth the distinctive characteristics of 'B9-65'. The present botanical description is that of 'B9-65' grown on an 8-year-old tree (Conserv Valencia block R14T36) growing on 'Carrizo' citrange rootstock (*C. sinensis*×*Poncirus trifoliata*) in Florida. The colors (except those in common terms) are described from The R.H.S. Colour Chart published by The Royal Horticultural Society in London (second edition), in association with the Flower Council of Holland.

Classification:

*Botanical.*—*Citrus sinensis.*

*Common name.*—Sweet orange.

Parentage: 'B9-65' is a somaclone of 'Valencia' sweet orange (*Citrus sinensis* L. Osbeck). The original plant was regenerated via adventitious shoot induction from a nucellar seedling internode stem segment on DBA3 shoot induction medium. The original tree, grafted to 'Carrizo' citrange, was planted in 1989 in a collaborative experimental block in Martin County.

Tree:

*Ploidy*.—Diploid.

*Size*.—Large.

*Tree height*.—6.5 to 7 m, or more if unpruned.

*Tree spread*.—5.5 to 6 m if unpruned.

*Vigor*.—Very vigorous, growing shoots of 40 cm or more, typically from strong spring flush on mature trees.

*Density*.—Canopies are quite dense.

*Form*.—The shape of the tree is obloid and branches grow toward upright; appears to exhibit more drooping after fruiting has commenced.

*Growth habit*.—Upright vegetative growth, drooping with fruit.

Trunk:

*Trunk diameter*.—Trunk diameter reaches 17 cm (at a height of 30 cm above the ground).

*Trunk texture*.—Smooth.

*Trunk bark color*.—RHS 197A (greyed-green); irregularly striated with RHS N200 (brown).

Branches:

*Crotch angle*.—Average tree crotch angle of 70 to 80 degree from the main trunk.

*Branch length*.—A typical branch can reach 6.5 meters from the first crotch point to the tip of leaf branch.

*Branch texture*.—Relatively smooth with small thorns or spines.

*Branch color* (*shoots from previous flush, hardened, and* 4 *to* 5 *mm in diameter*).—RHS 138A (green).

Leaves:

*Size* (*lamina average*).—Length: 107 mm. Width: 51 mm.

*L/W ratio*.—2.0 to 2.1.

*Thickness*.—Regular and average for commercial mandarin hybrids.

*Type*.—Simple.

*Shape*.—Elliptical.

*Apex*.—Very slightly retuse.

*Base*.—Acute to sub-obtuse.

*Margin*.—Entire, non-undulate.

*Surface*.—Upper surface: Glabrous. Lower surface: Medium veins that are pinnately netted.

*Color*.—Upper surface (adaxial): RHS 137A (green). Lower surface (abaxial): RHS 137C (green).

*Petiole*.—Shape: Brevipetiolate (shorter than leaf lamina); junction between petiole and lamina is articulate. Width (petiole wing): Narrow. Shape (petiole wing): Obovate. Length: 16 mm. Width: 3.5 mm. Color: RHS 137A (green).

Flowers and flower buds:

*Type*.—Hermaphrodite.

*Bearing*.—Flowers grow from leaf axillaries in clusters; each lower branch has 2-4 clusters.

*Flower diameter*.—Fully opened flowers have an average diameter of 46 mm.

*Flower depth*.—Typical flower depth between 21 to 22.8 mm.

*Flower blooming period*.—First bloom: Observed in Mid-March of 2010. Full bloom: Observed in late March to early April of 2010.

*Flower bud size*.—Length: 2.2 mm for the initial visible flower bud; 21.5 mm for mature flower buds before fully opening. Diameter: 2.2 mm for the initial visible flower bud; 8.3 mm for mature flower buds before fully opening.

*Flower bud shape*.—Round dome shape for initial visible flower bud; mature flower buds have an elongated olive shape.

*Color*.—RHS144D (yellow-green) for initial visible flower buds; RHSNN155B (white) for mature flower buds.

*Flower petals*.—Number: 5. Length: 23.6 mm on average. Width: 8.5 mm on average. Shape: Flat spatula shaped . Apex shape: Smooth with obtuse angle. Base shape: Even obtuse.

*Color*.—Upper surface: RHS 155C (white) to RHS 155B (white). Lower surface: RHSNN 155C (white) and RHS 150D (yellow-green) spot Distribution. Margin: Smooth.

*Sepal*.—Number (per flower): 4 to 5. Shape: Flat, spatula shaped. Length: 4.5 mm. Width: 3.0 mm. Apex shape: Acute angle at apex. Margin: Smooth.

*Color*.—Upper surface: RHS 144D (yellow-green). Lower surface: RHSN 144D (yellow-green).

*Fragrance*.—Fragrant compared to other citrus blossoms.

*Pedicel*.—Number: 1. Length: 9.7 to 10 mm on average. Diameter: 1.4 mm. Color: RHS 143B (green).

*Reproductive organs*.—Fertility: Self-fertile. Stamen Number: 20-21. Stamen length: 11.5 to 13.8 mm. Anther Length: 3.2 mm. Width: 1.0 mm. Color: RHS 13B (yellow). Filament length: 12.2 mm. Pollen amount: Abundant. Pollen color (general): RHS 17A (yellow). Pistil Number: 1. Length: 13.6 mm. Color: RHS 153C (yellow-green). Style length: 9.6 mm. Style diameter: 1.1 mm. Style color: RHS 143C (green). Ovary shape: Oval shaped. Ovary diameter: 3.5 mm. Ovary color: RHS143C (green).

Fruit:

*Average weight* (*per individual fruit*).—160 to 180 g.

*Size*.—Uniform, 73 to 80 mm in diameter, 78 to 83 mm tall.

*Width*.—Average of 73 to 80 mm.

*Length*.—Average of 78 to 83 mm.

*Shape*.—Round and earth shaped.

*Shape* (*cross-section*).—Round.

*Apex*.—Truncated.

*Apex cavity diameter*.—N/A.

*Base*.—No neck, slightly wrinkled surface.

*Base cavity diameter*.—5 to 5.2 mm.

*Harvesting*.—Same as typical commercial Valencia. Date of first harvest: Around mid-February (based on season and rootstock). Date of last harvest: Around mid-May (based on season and rootstock).

*Fruit stem*.—There are not specific or unique fruit stems, but a short stem connecting fruit body to the first knot of the fruit branch. Length: 5 mm. Diameter: 4.5 mm. Color: RHS 138A (green) with RHS 198D (greyed-green) strip distribution.

Skin:

*Adherence*.—Albedo (mesocarp) to flesh (endocarp) has strong adherence.

*Thickness*.—4 to 6 mm, medium thick compared to other commercial sweet oranges.

*Texture*.—Firm.

*Color*.—Flavedo (epicarp): Ranges between RHS 22B (yellow-orange) to RHS 23B (yellow-orange). Albedo (mesocarp): RHS 16D (yellow-orange). Stylar end: Closed.

*Rind oil cell density*.—Average 86 to 89 oil cells per square cm.

Flesh:

*Number of segments*.—Averages between 10 and 11 segments per fruit.

*Segment walls*—Medium soft.

*Juice*.—Abundant.

*Color*.—Uniformly RHS 23A (yellow-orange).

*Texture*.—Soft.

*Vesicles*.—Length: 12.3 to 13 mm on average.

*Diameter* (*thickness*).—1.8 to 2.0 mm on average.

*Juice quality* (*Juice quality analyzed in mid-April* 2009).—BRIX: 12.4. Soluble solids (per box): 6.2. Acidity (average): 0.9%. Sugar/Acid Ratio: 13.3.

Seeds:

*Type*.—Polyembryonic.

*Number*.—0 to 3 per fruit.

*Shape*.—Clavate to semi-deltoid.

*Size*.—Length: 14.5 mm. Width: 7.5 mm.

*Seed coat color*.—Outer Surface: RHS NN155A (white) and slightly wrinkled. Inner surface: RHS 165B (greyed-orange).

*Cotyledon color*.—RHS 155C (white).

Resistance to disease: Typical of 'Valencia' sweet orange.

What is claimed is:

1. A new and distinct cultivar of sweet orange tree as illustrated and described herein.

* * * * *